(12) United States Patent
MacKinnon et al.

(10) Patent No.: US 6,546,272 B1
(45) Date of Patent: Apr. 8, 2003

(54) APPARATUS FOR IN VIVO IMAGING OF THE RESPIRATORY TRACT AND OTHER INTERNAL ORGANS

(76) Inventors: Nicholas B. MacKinnon, 2267 Marstrand Ave., Vancouver, B.C. (CA), V6K 2H8; Stephen Lam, 5512 Wycliffe Road, Vancouver, B.C. (CA), V6T 2E5; Haishan Zeng, 1389 East 37th Ave., Vancouver, B.C. (CA), V5W 1G6; Calum E. MacAulay, 338 East 37th Ave., Vancouver, B.C. (CA), V5W 1E7

( * ) Notice: Subject to any disclaimer, the term of this patent is extended or adjusted under 35 U.S.C. 154(b) by 2 days.

(21) Appl. No.: 09/602,202

(22) Filed: Jun. 22, 2000

Related U.S. Application Data (60) Provisional application No. 60/140,885, filed on Jun. 24, 1999.

(51) Int. Cl.[7] .................................. A61B 5/00
(52) U.S. Cl. ...................... 600/407; 600/439; 600/466; 600/476; 600/478
(58) Field of Search ................ 600/407, 473, 600/476, 439, 437, 466, 472, 478, 160, 173, 182

(56) References Cited

U.S. PATENT DOCUMENTS

| | | | |
|---|---|---|---|
| 4,869,256 A * | 9/1989 | Kanno et al. ............... 348/163 |
| 5,321,501 A | 6/1994 | Swanson et al. ............ 356/345 |
| 5,452,088 A | 9/1995 | Ai ............................... 356/359 |
| 5,459,570 A | 10/1995 | Swanson et al. ............ 356/345 |
| 5,465,147 A | 11/1995 | Swanson ..................... 365/345 |
| 5,469,261 A | 11/1995 | Hellmuth et al. ........... 356/361 |
| 5,489,984 A | 2/1996 | Hariharan et al. .......... 356/360 |
| 5,491,524 A | 2/1996 | Hellmuth et al. ........... 351/212 |
| 5,493,109 A | 2/1996 | Wei et al. ................. 250/201.3 |
| 5,501,226 A | 3/1996 | Peterson et al. ............ 128/691 |
| 5,506,634 A | 4/1996 | Wei et al. ................... 351/221 |
| 5,537,162 A | 7/1996 | Hellmuth et al. ........... 351/206 |
| 5,543,914 A | 8/1996 | Henshaw et al. ........... 356/345 |
| 5,585,913 A | 12/1996 | Hariharan et al. ......... 356/4.09 |
| 5,644,642 A | 7/1997 | Kirschbaum ................ 382/103 |
| 5,710,630 A | 1/1998 | Essenpreis et al. ......... 356/345 |
| 5,757,763 A | 5/1998 | Green, Jr. et al. ....... 369/275.3 |
| 5,760,901 A | 6/1998 | Hill ............................. 356/345 |
| 5,778,016 A | 7/1998 | Sucha et al. .................. 372/38 |
| 5,784,352 A | 7/1998 | Swanson et al. .............. 369/94 |
| 5,813,988 A | 9/1998 | Alfano et al. ............... 600/476 |
| 5,835,642 A | 11/1998 | Gelikonov et al. ............ 385/4 |
| 5,867,268 A | 2/1999 | Gelikonov et al. ......... 356/345 |
| 6,035,229 A * | 3/2000 | Silverstein et al. ......... 600/117 |
| 6,191,862 B1 * | 2/2001 | Swanson et al. ............ 356/450 |
| 6,282,011 B1 * | 8/2001 | Tearney et al. ............. 359/287 |
| 6,294,775 B1 * | 9/2001 | Seibel et al. ............. 250/208.1 |

OTHER PUBLICATIONS

Sergeev, et al., "In vivo optical coherence tomography of human skin microstructure", Proc. SPIE, v. 2823, 1994, pp. 144–150.

(List continued on next page.)

*Primary Examiner*—Ruth S. Smith
(74) *Attorney, Agent, or Firm*—Christie, Parker & Hale, LLP (57) ABSTRACT

Apparatus for acquiring in vivo images of a site of interest within the internal organs of a body. The apparatus includes an elongate, flexible catheter. The catheter is introducible into the body and has a first end that remains external to the body and a second and positionable adjacent the site of interest. A movable scanning unit having at least one sensor for acquiring images is housed adjacent the second end of the catheter. There is a drive mechanism to control movement of the movable scanning unit from the first external end of the catheter to acquire multiple images of the site of interest. The drive mechanism has a control element extending the length of the catheter lumen adapted for linear movement within the lumen to generate linear or rotational movement of the scanning unit.

22 Claims, 6 Drawing Sheets

OTHER PUBLICATIONS

Sergeev, et al., "High–spatial–resolution optical–coherence tomography of human skin and mucous membrances", '95 Technical Digest, 1995, p. 349.

X. Clivaz, et al., "High–resolution reflectometry in biological tissues", Optics Letters, vol. 17, No. 1, Jan. 1, 1992, pp. 4–6.

J.A. Izatt, et al., "Micron–resolution biomedical imaging with optical coherence tomography", Optics & Photonics News, Oct. 1993, pp. 14–19.

E.A. Swanson, et al., "In vivo retinal imaging by optical coherence tomography", Optics Letters, vol. 18, No. 21, Nov. 1, 1993, pp. 1864–1866.

J.A. Izatt, et al., "Optical coherence microscopy in scattering media", Optics Letters, vol. 19, No. 8, Apr. 15, 1994 pp. 590–592.

V.M. Gelikonov, et al., "Coherent optical tomography of microscopic inhomogeneities in biological tissues", JETP Lett., vol. 61, No. 2, Jan. 25, 1995, pp. 158–162.

X.J. Wang, et al., "Characterization of human scalp hairs by optical low–coherence reflectometry", Optics Letters, vol. 20, No. 6, Mar. 15, 1995, pp. 524–526.

K. Takada, et al., "New measurement system for fault location in optical waveguide devices based on an interferometric technique", Applied Optics, vol. 26, No. 9, May 1, 1987, pp. 1603–1606.

C. Hitzenberger, "Optical Measurement of the Axial Eye Length by Laser Doppler Interferometry", Investigative Ophthalmology & Visuel Science, vol. 32, No. 3, Mar. 1991, pp. 616, 625.

* cited by examiner

FIG. 7

APPARATUS FOR IN VIVO IMAGING OF THE RESPIRATORY TRACT AND OTHER INTERNAL ORGANS

This application claims priority to Provisional Application Serial No. 60/140,885, filed Jun. 24, 1999.

FIELD OF THE INVENTION

This invention relates to an apparatus for acquiring in vivo medical images in real time at video rates utilizing optical, ultrasonic or opto-acoustical sensors.

BACKGROUND OF THE INVENTION

Various noninvasive medical imaging techniques have been developed for acquiring images of internal body organs for diagnostic purposes. These techniques generally involve introducing a catheter into the body and advancing it to the site of interest. Typically, a catheter equipped at its remote end with an imaging unit appropriate for the desired images would be inserted into the biopsy channel of a standard endoscopic device. Images are collected at the imaging unit and transmitted via optical fibre to image processing and analysis equipment external to the body.

Imaging techniques that utilize ultrasound, optical coherence tomography (OCT) or optical coherence microscopy (OCM) can reveal sub-surface biological structure providing benefits in the diagnosis of early cancer tumors and precise guidance for excisional biopsy.

Optical coherence tomography (OCT) is particularly desirable for in vivo imaging since it can provide tomographic images of sub-surface biological structure with approximately 4–10 μm resolution. It is analogous to ultrasound imaging in that two-dimensional images of structure are built up from sequential adjacent longitudinal scans of backscatter versus depth into the tissue. However, in OCT, the probing radiation is infrared light rather than sound waves, thus higher resolution measurements are possible. The usefulness of OCT has been well demonstrated in vitro on tissue samples and in vivo on easily accessed external organs such as the skin, teeth and eye. In addition, OCT has great potential for lung cancer detection, particularly for lesions located in the periphery airways where they cannot be reached by conventional endoscopes or catheters.

At present, in vivo imaging tends to be limited to larger organs that can readily accept a catheter. While small diameter catheters that could access smaller organs such as the peripheral airways of the lungs have been developed, size constraints continue to limit the functionality of the scanning heads of these catheters. In particular, small diameter catheters that include scanning units able to collected images at video rates are not yet available for access into organs such as the lung that has a complex branching system.

Conventional fibre-optic OCT systems employ a single rotating scan unit with image sensors at the distal end of the catheter which produce a radar-like scan of the site of interest. The scan unit is driven by a rotating wire or flexible drive-cable coupled to a motor at the end of the catheter external to the body. The configuration of the rotating drive element which extends the length of the catheter lumen creates a number of problems. Torsional flexing of the rotating drive element make it difficult to precisely control the position and speed of rotation of the scanning unit. In addition, friction and wear in the lumen of the catheter caused by this rotating element also adversely affect the operation and reliability of the apparatus. Rotational and frictional problems may be further exacerbated when the catheter is subjected to a tight bending radius.

In order to be appealing for in situ diagnostics, it must be possible to obtain near real-time imaging at video rates. Conventional catheters employing fibre-optic OCT technology use a single fibre and a single path interferometer to perform optical coherence tomography. Therefore, the frame rate is limited by the scanning rate of the reference arm of the interferometer. Furthermore, if contemplated, existing designs would be compelled to place additional elements in a coaxial configuration.

One of the best OCT systems developed to date utilizes a Fourier-domain rapid scanning optical delay line with a resonant scanner and performs 4000 A-scans per second (Rollins 1998) To run the system at video rates, only 125 A-scans per frame can be achieved, thus degrading the resolution of the images obtained. To obtain a high-resolution image of 500 A-scans per frame, only 8 frames per second of imaging can be performed. Faster scanning systems are being designed, but are not yet available.

Similar problems exist in endoscopic ultrasound where rotational scanning is used.

SUMMARY OF THE INVENTION

In view of the foregoing problems with existing catheter designs, it is apparent that there is a need for a new design that relies on an alternative scheme to drive the scanning unit and that permits imaging of internal organs in real time at video rates. It is also necessary for the catheter to be of sufficiently small diameter and sufficient flexibility to access small diameter regions of internal organs such as the lungs, coronary arteries, fallopian tubes or biliary ducts.

A novel apparatus for in vivo imaging has been developed that addresses the problems discussed above. Accordingly, the present invention provides apparatus for acquiring in vivo images of a site of interest within the internal organs of a body comprising:

an elongate, flexible catheter having a longitudinal axis and lumen defined by lumen walls, the catheter being introducible into the body and having a first end that remains external to the body and a second end positionable adjacent the site of interest;

a movable scanning unit having at least one sensor for acquiring images housed adjacent to the second end of the catheter;

communication means extending through the lumen of the catheter from the at least one sensor to communicate the sensor with the first end of the catheter;

a drive mechanism to control movement of the movable scanning unit from first external end of the catheter to acquire multiple images of the site of interest, the drive mechanism having a control element extending the length of the catheter lumen and adapted for linear movement within the lumen.

In a preferred embodiment, the apparatus of the present invention relies on a drive mechanism incorporating an actuating rod or wire that moves linearly within the lumen of the catheter to control movement of the scanning unit. The resulting movement of the scanning unit can be linear or rotational. This arrangement is not prone to the friction and wear problems of prior designs. Furthermore, the drive mechanism is flexible enough to operate without binding despite the tight radius of curvature that a catheter may experience when inserted into small diameter regions of internal organs such as the upper lobes of the lung.

The drive mechanism is extremely compact which permits the drive mechanism to be incorporated into extremely small diameter catheters for insertion into organs with small diameter passages. The drive mechanism is also relatively simple with few moving parts so that consistent, reliable operation is assured.

In addition, the apparatus of the present invention contemplates the use of a scanning unit having multiple sensors to increase the image acquisition rate. For OCT scanning, the image acquisition rate can be increased to over 30 frames per second while maintaining the high resolution of 500 A-scans per frame. An A-scan is the longitudinal or depth scan of the tissue being examined. This scan is generated by modulating the path length of the reference arm of the optical system, which produces a delay in the return of the reference signal. The use of a linearly movable control rod or wire to actuate the scan head removes the constraint of having coaxial optical fiber(s) as required by a rotating design. This permits additional fibre-optics to be incorporated in the lumen or lumens of the catheter.

BRIEF DESCRIPTION OF THE DRAWINGS

Aspects of the present invention are illustrated, merely by way of example, in the accompanying drawings in which.

DESCRIPTION OF THE PREFERRED EMBODIMENTS

In the following description, the apparatus of the present invention will be described primarily with respect to its use in association with equipment for optical coherence tomography (OCT), however, it will be appreciated by those skilled in the art that the apparatus of the present invention is suitable for use in other types of imaging operations. It is simply a matter of fitting the catheter of the present invention with a scanning unit appropriate for acquiring the desired images. It is intended that the apparatus of the present invention can also be used to acquire images using optical coherence microscopy (OCM), ultrasound or other suitable techniques.

Figure 1A:
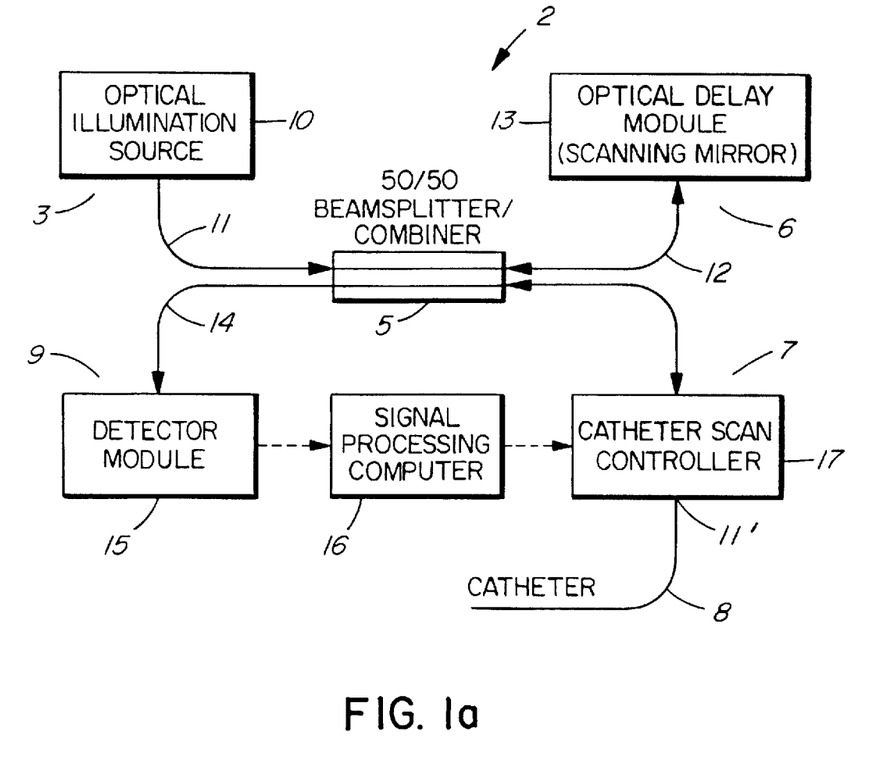
FIG. 1a is a schematic diagram showing an OCT system incorporating the catheter apparatus of the present invention equipped with a single sensor.

Referring to FIG. 1a, there is shown a schematic view of an OCT imaging system 2 that makes use of the apparatus of the present invention. The OCT imaging system 2 includes five main parts: an illumination arm 3, a beam splitter/combiner 5, a reference arm 6, a sample arm 7 that incorporates a catheter 8 for insertion into the body, and a detection arm 9.

The illumination arm 3 consists of a low coherence, broad band light source 10 and an optic fibre 11 to transmit illumination light from source 10 to a 50/50 beam splitter/combiner 5. The illumination light is divided by splitter/combiner 5 into two beams: one beam is transmitted to fibre 12 of the reference arm and the other beam is transmitted to sample arm 7 comprising an optic fibre in catheter 8. Reference arm 6 includes an optic delay module 13, essentially consisting of a moving mirror which generates a phase delayed reference beam. The optic fibre in catheter 8 delivers light to the site of interest within a subject's body via a sensor at the catheter tip. The reflected/backscattered light from the site of interest is collected in the optic fibre and delivered back to beam splitter/combiner 5. The sample beam and the reference beam are combined at beam splitter/combiner 5 and interfere if their time delay matches. The combined beam is then transmitted via optic fibre 14 to detector module 15 of detection arm 9. The detected signal is demodulated and processed by signal processing computer 16 to generate an intensity profile of the reflected/backscattered light as a function of the tissue depth (corresponding to an A-scan in ultrasound imaging). A cross-sectional image is produced by scanning the light beam across the tissue while the A-scan profiles at each transverse position are recorded by the computer. The beam scanning can be performed radially, perpendicular to the longitudinal axis of catheter 8, or linearly along the catheter axis depending on the design of the scanning unit at the distal end of the catheter as will be discussed below. The movement of the scanning unit is controlled by catheter scan controller 17.

Figure 1B:
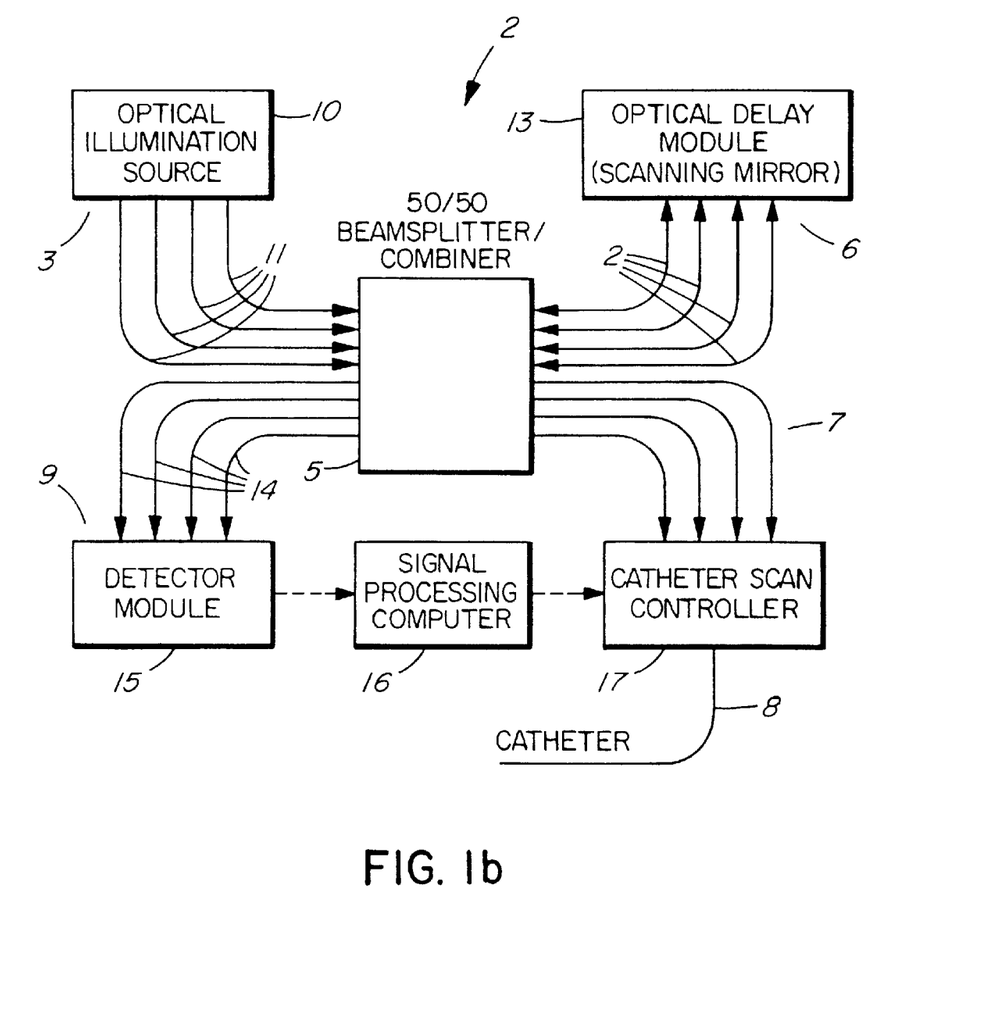
FIG. 1b is a schematic diagram of an OCT system incorporating the catheter apparatus of the present invention that is set up to accommodate multiple sensors and employs a single interferometer.
Figure 1C:
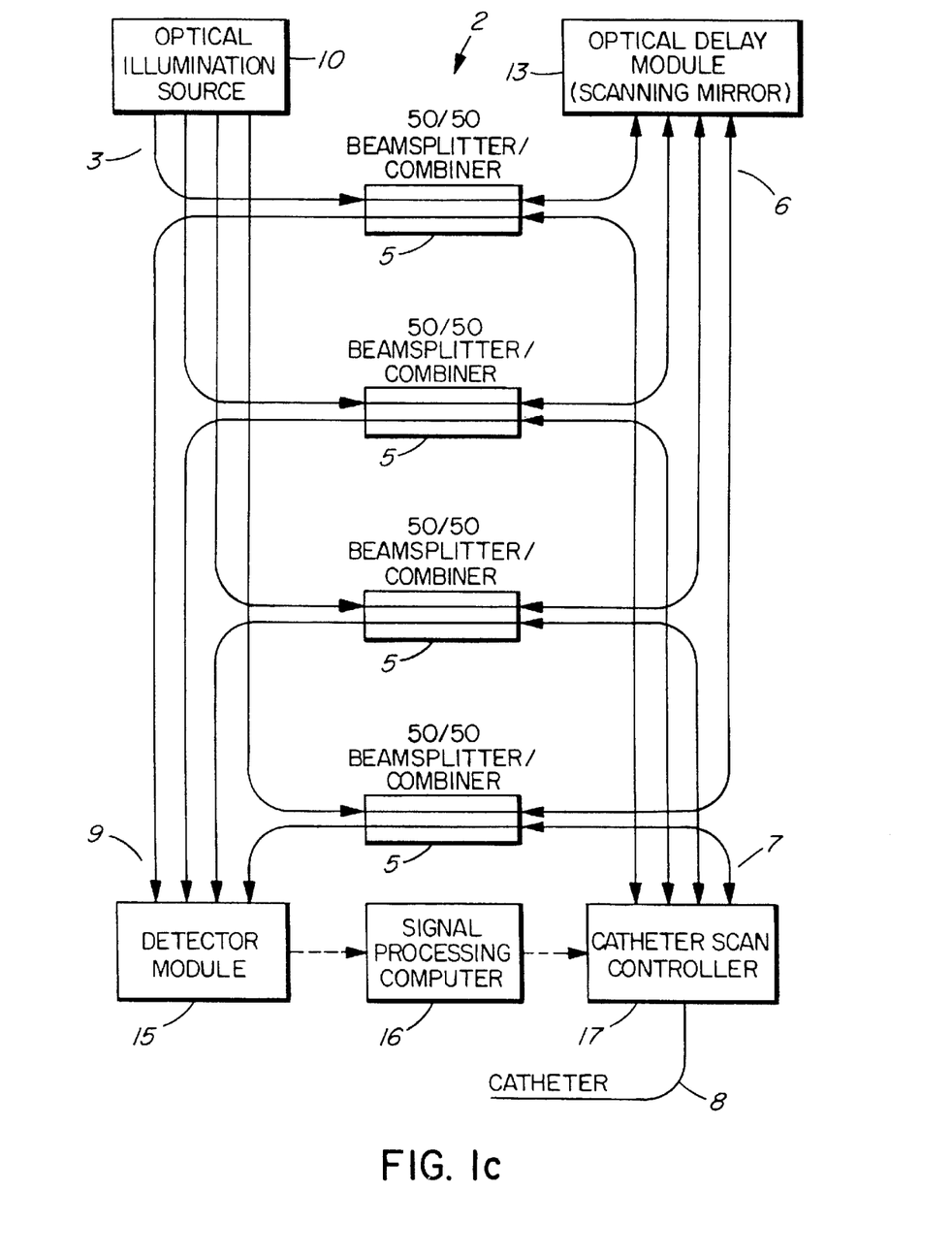
FIG. 1c is a schematic diagram of an OCT system similar to that shown in FIG. 1b with multiple sensors in the catheter and multiple interferometers.

FIGS. 1b and 1c are block diagrams of alternative OCT imaging systems in which identical parts to the system of FIG. 1a are labeled with the same reference numbers.

FIG. 1b shows an OCT imaging system that uses multiple optic fibres in communication with multiple sensors within catheter 8. This arrangement is suited to fast image acquisition. As will be explained in more detail below, the catheter 8 of FIG. 1b is equipped with four sensors. Therefore, four optic fibres are needed to transmit light between the various arms of the imaging system, one optic fibre being in communication with each sensor. For example, four illumination fibres 11 conduct light from optical illumination source (or sources) 10 to separate input positions of the beam splitter/combiner 5. Each input beam is divided into two beams with one beam going to reference arm 6 via its own fibre 12 and the other beam going to sample arm 7 via its own fibre. The four fibres 12 in reference arm 7 feed into optical delay module, 13 separately. Alternatively, if space is limited, fibres 12 can be fused together and fed into delay module together. In either arrangement, four reference beams are generated and fed back into the beam splitter/combiner 5. The four fibres in sampling arm 7 are connected to four sensors at the scanning unit of catheter 8 to acquire simultaneous images of the site of interest. Each of the four sample beams returned by the four optic fibres of the catheter is fed into the beam spl-tter/combiner 5 and combined with one of the four reference beams. Each of the four combined beams is then received by one of the four optic fibres 14 of the detection arm 9. Four detectors are provided in detector module 15 to receive the signal from optic fibres 14. Computer 16 generates four images simultaneously and combines them together to form a single image.

FIG. 1c is a variation of the OCT imaging system of FIG. 1b in which four separate beam splitters/combiners 5 are used instead of a single unit.

Figure 2:
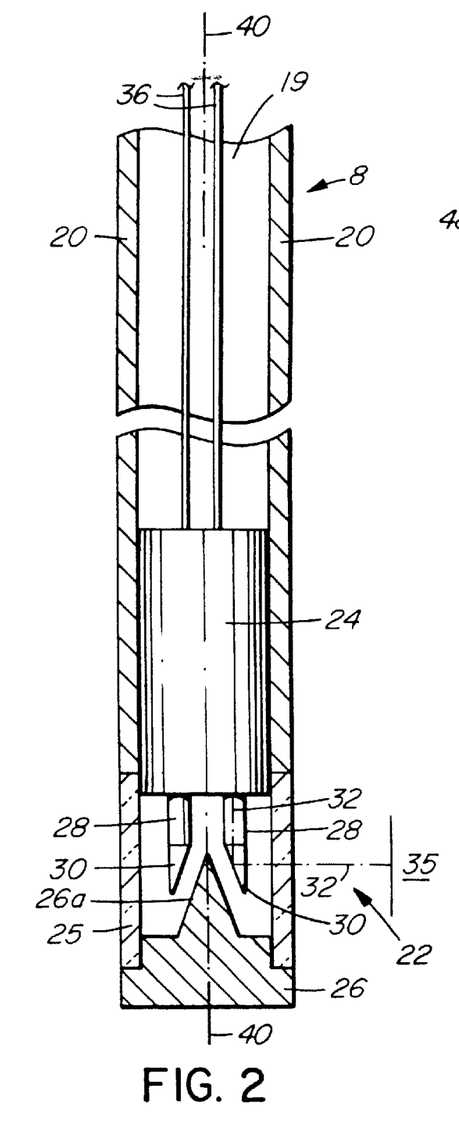
FIG. 2 is a detail cross-sectional view of the catheter adjacent the second end.

In all the OCT imaging system described above, light is delivered to and reflected back from the site of interest via catheter 8. Catheter 8 is connected to catheter scan controller 17 by a first end 11'. When examining the lungs, catheter 8 preferably passes through the biopsy channel of a standard bronchoscope. lo fit the channel, catheter 8 must be less than 2 mm in diameter. For insertion into the peripheral airways of the lung, the catheter is preferably less than 1 mm in diameter. A schematic cross-section view of the general structure of catheter 8 is shown in FIG. 2. Catheter 8 comprises an elongate, flexible tube having a longitudinal axis and lumen 19 defined by lumen walls 20. The second internal end 22 of catheter 8 houses movable scanning unit 24 which includes at least one sensor 28 for acquiring images of the site of interest. A drive mechanism is provided to move scanning unit 24 within catheter 8 to perform scanning passes of the site of interest.

Sensor 28 is selected for the type of imaging to be conducted. For example, for acquiring OCT images, sensor 28 preferably comprises a combination micro GRIN (Gradient Refractive index) lens/prism element 30 that acts to deflect the optical path 32 ninety degrees through a transparent annular window 25 towards the site of interest 35 external to the catheter. Window 25 is adjacant the second end 22 of catheter 8.

Figure 3:
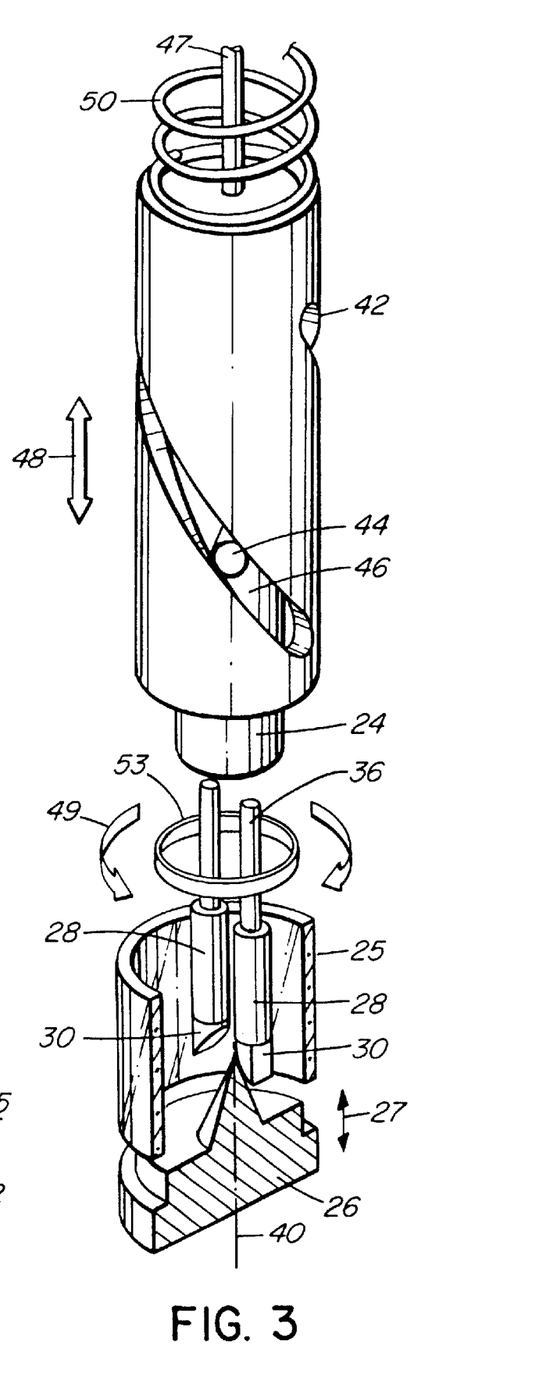
FIG. 3 is a detail view of the scanning unit and drive mechanism of the apparatus of the present invention according to a first embodiment suitable for rotational scanning of the site of interest.

In the case of OCM scanning, sensor 28 includes a diffractive lens or conventional lens to precisely focus the beam to a point of focus at a site of interest. As shown in FIGS. 2 and 3, end 22 of catheter 28 is preferably sealed with an end cap 26 that includes an inwardly extending conical protrusion 26a which is used to achieve depth scanning of the point of focus. Conical protrusion 26a of catheter cap 26 is movable relative to sensors 28 to engage and move the sensors in a radial direction in relation to the longitudinal axis 40 of the catheter thereby permitting adjustment of the depth of the point of focus at the site of interest. Movement of conical protrusion 26a is accomplished by mechanical or piezo-electric actuators at the end cap.

The sensors that can be used with the apparatus of the present invention are not limited to optical sensors. For ultrasound scanning, sensors 28 comprise conventional ultrasound sensors consisting of a piezo-electric crystal that vibrates at a particular frequency when a voltage waveform is applied to it and/or generates a voltage waveform when ultrasonic energy is applied to it. Sometimes, the same crystal is used for generation of the ultrasonic pulse and detection of the returning echo.

In fact, the apparatus of the present invention can be used with any type of sensor that can emit and detect an energy beam. In general, sensor 28 is a point sensor that is movable by the apparatus of the present invention for scanning across a site of interest to collect image data for assembly into a digital image. Additional imaging techniques that can be carried out using the apparatus of the present invention equipped with an appropriate sensor 28 include optical reflectance, Raman spectral measurement, fluorescence spectral or discrete wavelength(s) measurement or opto-acoustic measurements. In the latter technique, a laser or other form of light energy is directed into tissue to create a microbubble of gas or plasma. When the bubble collapses, an ultrasound pulse is generated which is measured by a piezo-electric crystal detector.

In the case of OCM or OCT scanning, optical sensors 28 are positioned at the end of optic fibres 36 that extend through the lumen 19 of catheter 8 and act to communicate the sensors with the first end of the catheter. For other sensors, appropriate connection fibres communicate the sensor with the first end of the catheter through the lumen of the catheter. For example, an ultrasound sensor will communicate via a signal wire that carries the signal generated by sensor.

FIG. 3 is a detail view showing a first embodiment of the apparatus of the present invention that is particularly suited for use in OCT scanning that incorporates a drive mechanism for achieving rotational movement of scanning unit 24 about the longitudinal axis 40 of the catheter. The drive mechanism includes a movable sleeve 42 mounted within the catheter lumen proximate the second end 22 of the catheter. Scanning unit 24 includes a generally cylindrical body that is positioned within the interior of sleeve 42. Optical sensors 28 (GRIN lens elements) extend along the longitudinal axis of the catheter from the body of scanning unit 24 to be adjacent window 25. The optic fibres 36 associated with sensors 28 are retained in channels that extend through the scanning unit body. A plurality of projections 44 extend radially outwardly from the cylindrical body of scanning unit 24 and are retained in helical channels 46 formed in the walls of sleeve 42. A control element in the form of a flexible linear rod or wire 47 extends the length of the catheter lumen and is connected to movable sleeve 42. Preferably, for the majority of its length through catheter 8, control element 47 is slidably housed in a cavity within the lumen wall. Adjacent second end 22 of the catheter, control element emerges from the cavity to connect to sleeve 42. Linear movement of the control element 47 at the first external end of the catheter results in corresponding movement of sleeve 42 within the walls of catheter lumen 19 as indicated by arrow 48. The linear movement of sleeve 42 moves helical channels 46 in the sleeve which forces corresponding movement of projections 44 retained in the channels. The result is reciprocating rotational movement of scanning unit 24 about the longitudinal axis 40 of the catheter as indicated by arrows 49. Back and forth movement of control element 47 results in attached sensors 28 following an annular scan path at the site of interest in a plane at right angles to the longitudinal axis of the catheter.

Preferably, the drive mechanism of the present invention includes biasing means to ensure that control element 47 is maintained in tension during operation. For example, in the embodiment of FIG. 3, a coiled biasing spring is provided to engage with sleeve 42 and bias the sleeve toward the second end of the catheter. Any movement of control element 47 is performed against the restoring force exerted by spring 50.

While the illustrated embodiment shows projections 44 on the scanner unit body and helical channels in movable sleeve 42, it will be readily apparent to a person skilled in the art that other arrangements of the projections and channels are possible to achieve the desired relative movements of the scanning unit body and the sleeve. For example, radially inwardly extending projections can be formed on the inner wall of sleeve 42 to be slidably retained in helical channels formed in the cylindrical walls of the scanning body. Alternatively, a helically twisted elongate element can be pushed linearly through a slot in the scanning unit to rotatably drive the scanning unit or a slotted opening can be driven linearly along a helically twisted elongate element rigidly attached to the scanning unit.

The illustrated embodiments show a single control element 47. It will be appreciated that the apparatus of the present invention can also accommodate two or more control elements to ensure balanced forces to cause movement of scanning unit 24.

The important common factor of all the above described actuating means is that at least one linearly moving control rod is manipulated to achieve rotary movement of the scanning unit. This arrangement avoids the drive schemes of prior art systems, which rely on a rotating drive element that extends the full length of the catheter.

The angle through which scanning unit body 24 rotates to complete a full 360 degree scan is determined by the number of sensors 28. FIG. 3 shows an arrangement in which there are two sensors 28, and in order to perform a full 360 degree field of view scan each sensor must rotate through 180 degrees. Therefore, in the embodiment shown in FIG. 3, helical channels 46 in sleeve 42 are dimensioned to permit rotation of the scanning unit through 180 degrees.

Figure 4:
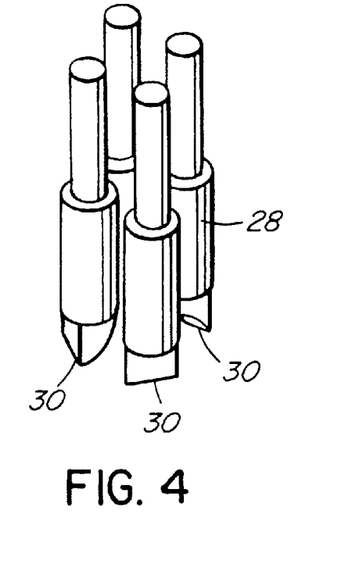
FIG. 4 is a detail view of an arrangement of the sensors.

FIG. 4 shows the manner in which four sensors 28 can be positioned symmetrically about the longitudinal axis of a scanning unit which is co-axial with the axis of the catheter. In this arrangement, each sensor must rotate through ninety degrees to complete a full 360 degree scan. Therefore, in order to perform a full 360 degree scan, the drive mechanism must be designed to rotate scanning unit 24 through an angle of about 360/n degrees where n is the number of sensors. It may be desirable in some cases to over-scan or under-scan the field of view of individual sensors to facilitate image reconstruction so that the actual scan angle may be more or less than 360/n degrees.

The rotary movement of the scanning unit of the present invention is achieved by reciprocating movement of the scanner through at most 360 degrees. Sufficient slack is provided in the optic fibres 36 that extend from scanning unit 24 to the first end of the catheter to accommodate such movement.

Passing a beam of light through a curved optical element such annular window 25 will tend to introduce some optical distortion to the light beam emanating from or being collected by a particular sensor 28. This type of cylindrical distortion can be readily corrected by providing a compensating curvature or Fresnel type micro-structure to the reflecting or emitting surface of the prism element 30.

Figure 5:
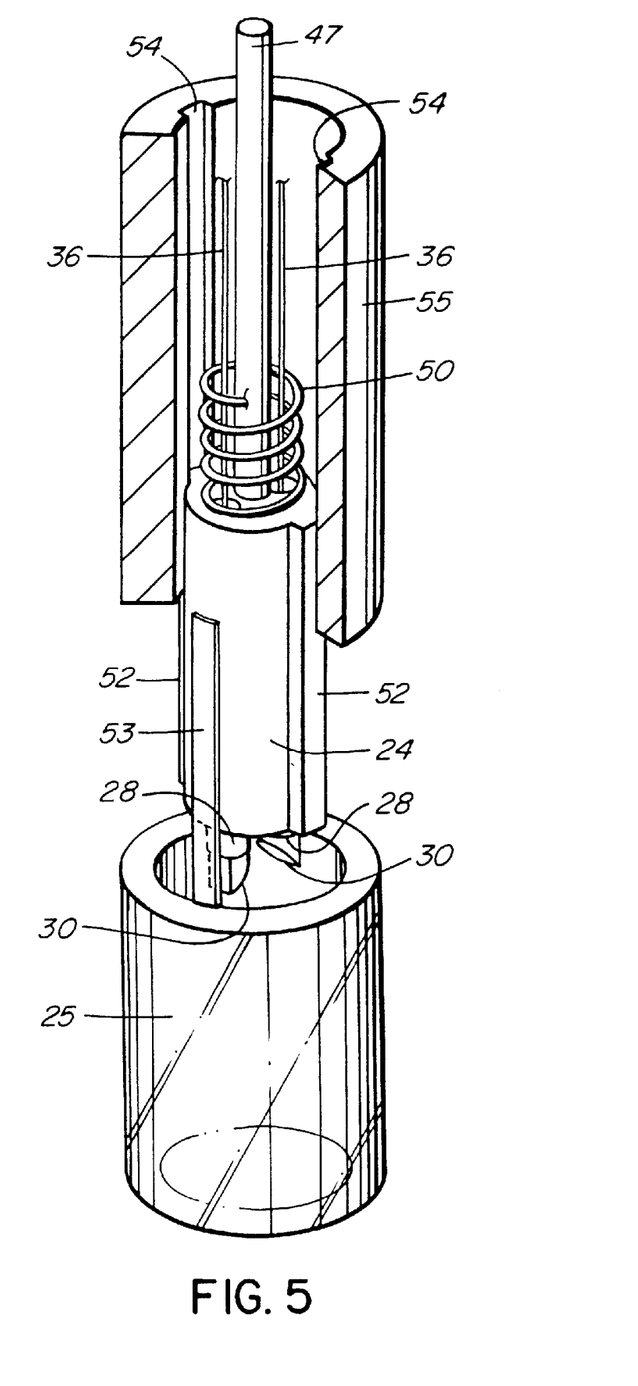
FIG. 5 is a detail view of the scanning unit and drive mechanism of a second embodiment suitable for linear scanning of a site of interest.

FIG. 5 is a detail view showing a second embodiment of the apparatus of the present invention that incorporates a drive mechanism for achieving linear movement of scanning unit 24 along the longitudinal axis of the catheter. In this case, the drive mechanism includes flanges 52 and corresponding channels 54 formed in either the scanning unit or the lumen walls of the catheter. The flanges are slidably retained in the channels. The control element is in the form of a flexible rod or wire 47 extending the length of the catheter lumen and connected to scanning unit 24. Linear back and forth movement of control element 47 results in corresponding linear movement of scanning unit 24 guided by flanges 52 traveling in channels 54 to obtain a linear scan at the site of interest for each sensor 28 parallel to the longitudinal axis of the catheter. Two sensors 28 with associated optic fibres 36 are shown in FIG. 5, however, a single sensor or more than two sensors can be used. A stationary sleeve 55 mounted within the catheter lumen proximate the second end of the catheter is preferably formed with channels 54 or flanges 52. Alternatively, the channels or flanges can be formed directly in the lumen walls of the catheter with the corresponding structure being formed on the scanning unit 24.

Coil spring So is provided to exert a biasing force on scanning unit 24 to move the unit toward the second end of the catheter to maintain tension in control element 47 to ensure reliable operation of the apparatus of the present invention.

With the linear scanning arrangement described above, window 25 is dimensioned to be of sufficient length to accommodate the linear movement of the scanning unit.

Figure 6:
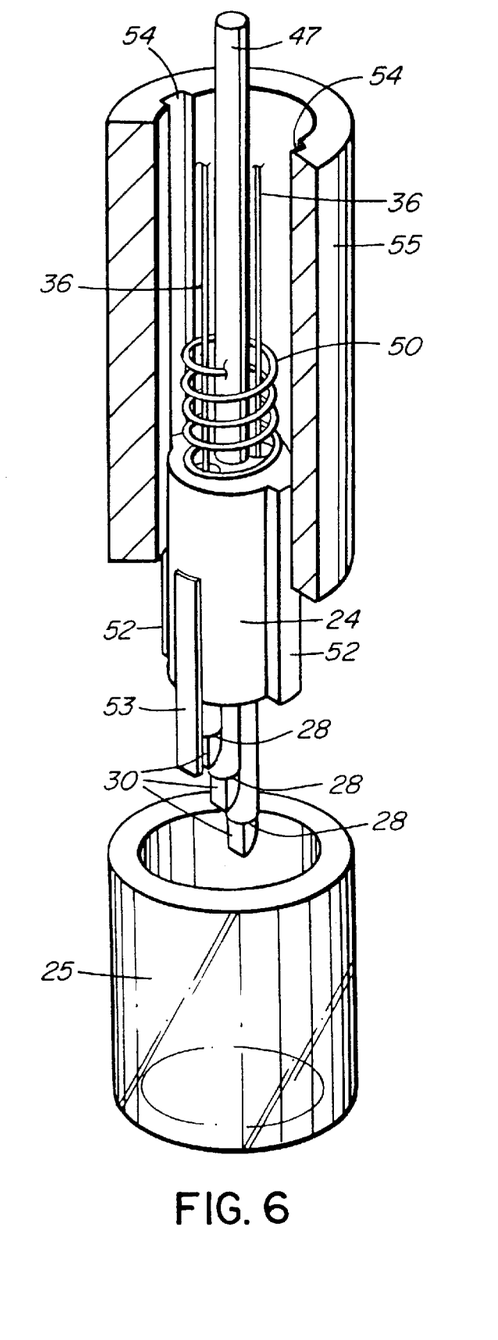
FIG. 6 is detail view of the scanning unit and drive mechanism of a second embodiment suitable for linear scanning of a site of interest.

Multiple sensors can be mounted in a radial array as illustrated in FIG. 5 or as an axially extending linear array as shown in FIG. 6. If multiple sensors are mounted as an axially extending linear array, the distance the scanning unit is required to travel to obtain a complete image can be reduced to D/n where D is the scan length of the site of interest and n is the number of sensors distributed along the scan length.

To assist in accurate movement and linear positioning of the scanning unit 24 in the embodiments of FIGS. 5 and 6, one of the multiple fibres 36 and attached sensors 28 can be used in conjunction with an optical encoder scale 53 at the catheter tip to measure the precise position of the scanning unit. A similar encoding scale 53 can be used to measure the radial travel in the rotational scanning embodiment of FIG. 3.

In a multiple sensor, linear scanning arrangement of the present invention, it is anticipated that different sensors can be used to scan at different wavelengths of light to provide additional information about the site of interest.

The drive mechanism of the present invention provides a simple and reliable arrangement that is an elegant solution to the problem of performing accurate scanning of a site of interest at a remote location within the interior of the body. Control element 47 is sufficiently flexible to accommodate extreme flexing of the catheter and tight radius of curvature bending that is often necessary to insert the catheter into small diameter regions of the lungs or other organs. The drive mechanism to generate rotation of the scanning unit allows a user to view any portion of the site of interest without having to rotate the catheter. Further, the rotary scanning embodiment of the present invention with multiple sensors allows collection of sufficient data to generate images at video rates of up to 30 frames per second. The scan mechanism is also fast enough to be minimally affected by movement of the site of interest caused by normal body functions such as breathing or proximity to the beating heart.

As previously explained and illustrated in FIGS. 1a, 1b and 1c, the first end 11 of the catheter of the present invention external to the body communicates with an imaging system which receives and processes the image data collected by sensors 28 at the second end of the catheter. Due to the novel drive system of the present apparatus for moving scanning unit 24, it is possible for the first end of catheter 8 to be fixed in position relative to the imaging system to which it is connected. Therefore, unlike prior art catheter designs, which employ an axially rotating control element extending the length of the catheter, the apparatus of the present invention is not limited to a single communication fibre that must be rotatably mounted to the detector unit to accommodate rotary movement of the control element. Instead, the apparatus of the present invention can accommodate multiple sensors and multiple associated communication fibres that are arrayed and collimated to direct multiple parallel signals into the interferometer portion of the imaging system. This parallel processing allows for a large amount of image information to be collected in a shorter time.

Even though the catheter apparatus of the present invention is able to provide detailed in viva images of the site of interest for diagnostic purposes, it is still desirable to be able to conduct a biopsy of the site to obtain a sample that can be analyzed using conventional diagnostic tests and techniques. Preferably, the scanning unit 24 of the catheter is removable from the lumen of catheter 8. The scanning unit with attached sensors and communication fibres is removed by applying an extraction force via control element 47. The empty lumen of catheter 8 defines a passage to the site of interest for a conventional biopsy tool such as a brush or biopsy forceps. The cap at the end of the catheter is removable to allow access to the exterior of the lumen.

Figure 7:
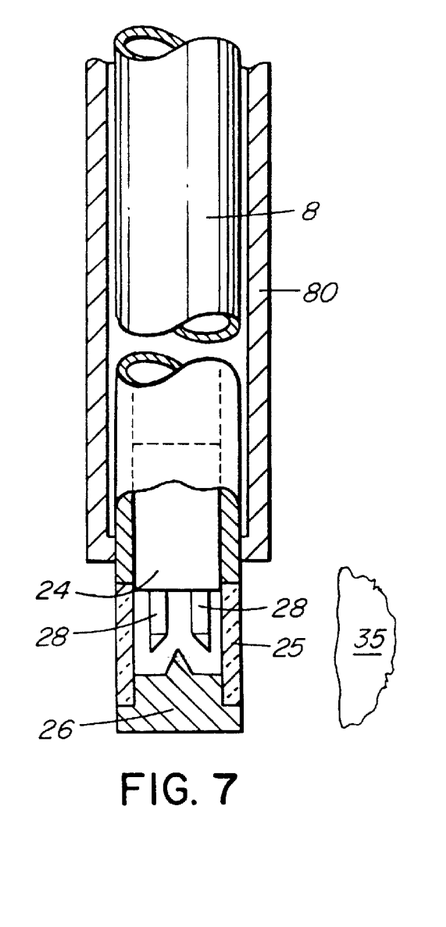
FIG. 7 is a detail view of the internal second end of the catheter showing a further embodiment capable of performing biopsy sampling at the site of interest.

In an alternative arrangement illustrated in FIG. 7, the apparatus of the present invention includes an outer sleeve or sheath 80 that extends over the length of the catheter from first end 11 to immediately adjacent window 25 at the second end of the catheter. The end of sleeve 80 adjacent window 25 includes a seal. This arrangement allows for normal radial or linear scanning operation of scanning unit 24 through window 25 which protrudes from the end of sleeve 80. When a biopsy sample is required, catheter 8 is withdrawn from sleeve 80 such that the sleeve defines a passage for a biopsy tool to be inserted directly to the site of interest.

Although the present invention has been described in some detail by way of example for purposes of clarity and understanding, it will be apparent that certain changes and modifications may be practiced within the scope of the appended claims.

We claim:

1. Apparatus for acquiring in vivo images of a site of interest within the internal organs of a body comprising:
   an elongate, flexible catheter having a longitudinal axis and a lumen defined by lumen walls extending along a length of the catheter, the catheter being introducible into the body and having a first end that remains external to the body and a second end positionable adjacent the site of interest;
   a movable scanning unit having at least one sensor for acquiring images housed adjacent to the second end of the catheter;
   communication means extending through the lumen of the catheter from the at least one sensor to communicate a signal from the,sensor to the first end of the catheter;
   a drive mechanism to control movement of the movable scanning unit from the first external end of the catheter to acquire at least one image of the site of interest, the drive mechanism having a control element extending the length of the catheter lumen and adapted for linear movement within the lumen.

2. Apparatus as claimed in claim 1 in which the drive mechanism causes reciprocal rotational movement of the scanning unit about the longitudinal axis of the catheter.

3. Apparatus as claimed in claim 2 in which the drive mechanism comprises:
   a movable sleeve mounted within the lumen proximate the second end of the catheter;
   at least one projection and a corresponding helical channel formed on one of the scanning unit and the movable sleeve, the projection of one being slidably retained in the helical channel of the other;
   the control element being at least one linear rod extending the lenath of the catheter lumen and connected to the movable sleeve whereby linear movement of the rod and sleeve is converted to rotational movement of the scanning unit about the longitudinal axis of the catheter by movement of the projection in the helical channel.

4. Apparatus as claimed in claim 3 including a window at the second end of the catheter for the at least one sensor of the scanning unit to acquire images of the site of interest.

5. Apparatus as claimed in claim 3 in which the helical channels are dimensioned to permit rotation of scanning unit through an angle or about 360/n where n is the number of sensors.

6. Apparatus as claimed in claim 1 in which the drive mechanism causes linear movement of The scanning unit along the longitudinal axis of the catheter.

7. Apparatus as claimed in claim 6 in which the at least one sensor comprises a linear array of sensors extending parallel to the longitudinal axis of the catheter.

8. Apparatus as claimed in claim 6 in which the drive mechanism comprises:
   at least one flange and a corresponding channel formed on one of the scanning unit and the lumen walls of the catheter, the flange of one being slidably retained in the channel of the other;
   the control element being at least one rod extending the length of the catheter lumen and affixed to the scanning unit whereby linear movement of the rod results in movement of the scanning unit as guided by the flanges traveling in the channels.

9. Apparatus as claimed in claim 6 including a window at the second end of the catheter for the at least one sensor of the scanning unit to acquire images of the site of interest, the window being of sufficient length to accommodate the linear movement of the scanning unit.

10. Apparatus as claimed in claim 8 including a stationary sleeve mounted within the lumen proximate the second end of the catheter and formed with one of the flanges and channels.

11. Apparatus as claimed in claim 1 in which the at least one sensor is an optical sensor.

12. Apparatus as claimed in claim 11 in which the communication means comprises an optic fibre associated with the optical sensor.

13. Apparatus as claimed in claim 11 in which the optical sensor comprises a micro GRIN lens/prism element adapted to obtain optical coherence tomography (OCT) images.

14. Apparatus as claimed in claim 11 in which the optical sensor comprises a diffractive lens to focus light to a point of focus adapted to obtain optical coherence microscopy (OCM) images.

15. Apparatus as claimed in claim 14 including means to adjust the depth of focus of the optical sensor at the site of interest.

16. Apparatus as claimed in claim 15 in which the means to adjust the depth of focus comprises a movable conical protrusion adjacent to the second end of the catheter movable along the longitudinal axis of the catheter to engage and displace the ar least one sensor in a radial direction in relation to the longitudinal axis of the catheter.

17. Apparatus as claimed in claim 1 in which the at least one sensor is an ultrasound sensor.

18. Apparatus as claimed in claim 17 in which the communication means comprises a wire to carry the signal generated by the ultrasound sensor.

19. Apparatus as claimed in claim 1 including means to maintain the control element in tension within the catheter lumen.

20. Apparatus as claimed in claim 1 including tracking means to monitor the position of the movable scanning unit.

21. Apparatus as claimed in claim 1 in which the scanning unit is removable from the lumen of the catheter to permit introduction of a biopsy too through the catheter lumen for sampling at the site of interest.

22. Apparatus as claimed in claim 1 including a window at the second end of the catheter For the at least one sensor of the scanning unit to acquire images of the site o-f interest and an outer sleeve extending over the length of the catheter from the first end to adjacent the window at the second end whereby the catheter is removable from the sleeve and the interior of the sleeve defines a passage to the site of interest for introduction of a biopsy tool.

* * * * *

UNITED STATES PATENT AND TRADEMARK OFFICE
CERTIFICATE OF CORRECTION

PATENT NO. : 6,546,272 B1 Page 1 of 1
DATED : April 8, 2003
INVENTOR(S) : Nicholas B. MacKinnon et al.

It is certified that error appears in the above-identified patent and that said Letters Patent is hereby corrected as shown below:

Column 9,
Line 44, replaec "the,sensor" with -- the sensor --;
Line 63, replace "lenath" with -- length --

Column 10,
Line 6, replace "or" with -- of --;
Line 9, replace "The" with -- the --;
Line 53, replace "ar" with -- at --;
Line 66, replace "too" with -- tool --.

Column 11,
Line 2, replace "For" with -- for --;
Line 3, replace "o-f" with -- of --.

Signed and Sealed this

Twenty-ninth Day of June, 2004

JON W. DUDAS
*Acting Director of the United States Patent and Trademark Office*